United States Patent
Bobbert

(10) Patent No.: US 8,048,930 B2
(45) Date of Patent: Nov. 1, 2011

(54) ACTIVATED PEROXIDE SOLUTIONS AND A PROCESS FOR THE PREPARATION THEREOF

(75) Inventor: Ilja Bobbert, Hilversum (NL)

(73) Assignee: Aseptix Technologies B.V., Bredestraat (NL)

( * ) Notice: Subject to any disclaimer, the term of this patent is extended or adjusted under 35 U.S.C. 154(b) by 214 days.

(21) Appl. No.: 12/084,124

(22) PCT Filed: Oct. 25, 2006

(86) PCT No.: PCT/EP2006/067767
§ 371 (c)(1),
(2), (4) Date: Jun. 3, 2008

(87) PCT Pub. No.: WO2007/048808
PCT Pub. Date: May 3, 2007

(65) Prior Publication Data
US 2009/0098062 A1    Apr. 16, 2009

(30) Foreign Application Priority Data
Oct. 25, 2005    (EP) .................... 05109972

(51) Int. Cl.
*A01N 25/02*    (2006.01)
*A61K 47/02*    (2006.01)
(52) U.S. Cl. ..................................... 514/769
(58) Field of Classification Search .................. None
See application file for complete search history.

(56) References Cited

U.S. PATENT DOCUMENTS
4,477,438 A * 10/1984 Willcockson et al. ........ 424/616
2003/0146310 A1    8/2003 Jackson

FOREIGN PATENT DOCUMENTS
WO    WO 02/059046 A2    8/2002

OTHER PUBLICATIONS
May 3, 2010 European Office Action issued in European Patent Application No. 06 819 142.8.

\* cited by examiner

*Primary Examiner* — James H Alstrum Acevedo
*Assistant Examiner* — Jessica Kassa
(74) *Attorney, Agent, or Firm* — Oliff & Berridge, PLC

(57) ABSTRACT

The present invention discloses an activated biocidal aqueous solution containing hydrogen peroxide (activated peroxide solution) obtainable by subjecting an initial solution of hydrogen peroxide in water to a non-thermal electrical discharge process, such as a glow discharge plasma or a corona discharge. The resulting activated peroxide solution containing 0.05 to 20% (w/w) hydrogen peroxide has a pH in the range of 2 to 4, an oxidation-reduction potential (ORP) in the range of 400 to 600 mV, and the solution when having a peroxide content in the range of 0.05% to 0.5% (w/w) has a conductivity in the range of 100 to 500 µSiemens/cm, the solution when having a peroxide content in the range of 0.1% to 5% (w/w) has a conductivity in the range of 100 to 450 µSiemens/cm, and the solution when having a peroxide content in the range of 5% to 20% (w/w) has a conductivity in the range of 100 to 350 µSiemens/cm. The pH, ORP and conductivity are measurable under conditions essentially without the presence of additional compounds in the solution. The biocidal activity of the solution is substantially higher than that of a common peroxide solution. The biocidal solution may be used for any purpose where disinfecting and/or sanitizing and/or cleaning and/or bleaching and/or preservative activity is required. The present invention further discloses a non-thermal electrical discharge process, in particular a pulsed corona induced low frequency pulsed DC plasma discharge process, for the preparation of the activated peroxide solution.

22 Claims, No Drawings

ACTIVATED PEROXIDE SOLUTIONS AND A PROCESS FOR THE PREPARATION THEREOF

The present invention relates to environmentally friendly and safe biocidal solutions comprising hydrogen peroxide.

Hydrogen peroxide ($H_2O_2$) is known to possess broad germicidal properties with an ability to kill organisms through oxidative action. At lower concentrations (e.g., below 6%), it is safe to handle and is considered environmentally friendly because it readily decomposes into oxygen and water. One disadvantage is that at such lower concentrations its rate of disinfection or its killing rate may be rather low. Although the disinfection rate or killing rate may be increased simply by increasing the $H_2O_2$ concentration, this goes at the expense of safety because more concentrated $H_2O_2$ solutions are also strong oxidizing agents. For example, at concentrations above about 8% (w/w) aqueous solution, hydrogen peroxide is considered corrosive, irritating and bleaching.

A water-soluble acid may be combined with $H_2O_2$ to improve its efficacy. This approach has been used by some manufacturers of peroxide-based disinfectants, who have added a second active agent, especially an acid such as phosphoric acid, peracetic acid, acetic acid, a food grade acid, benzoic acid, mixtures of several acids, to $H_2O_2$. However, these combinations of peroxide and acid still require relatively long contact times to achieve high level disinfection (e.g., more than 5 minutes) and are often corrosive. They also have poor material compatibility because of their very low pH (typically lower than 2) and oxidizing ability. Many of these acids are not only environmentally unsafe, they also leave environmentally unfriendly residues. Thus, to overcome the slow effectiveness of peroxide mixtures, peroxide mixtures described as a disinfection agent, biocidal solution or sanitization agent need the addition of organic or inorganic acids to lower the pH to levels that make the hydrogen peroxide active at lower concentrations. Shorter disinfection times have been reported for formulations that combine an acid such as succinic acid with a higher level of peroxide, e.g. 13.4%, thus negating the attractive safety feature of a more dilute $H_2O_2$ solution.

Most if not all peroxygen-based mixtures used for cleaning and disinfection either suffer from impractically long contact times or unfeasibly high hydrogen peroxide concentrations.

The objective of the present invention is to provide for low concentrated hydrogen peroxide based biocidal solutions that exhibit practical biocidal activity without the need to add complex chemical mixtures for reaching practical utility of the solutions.

Applicant found that by subjecting a hydrogen peroxide solution to a non-thermal electrical discharge, such as a plasma discharge or a corona discharge, it was possible to reach practical contact times of the resulting solution without the need to add hazardous chemicals or use excessively high and corrosive levels of hydrogen peroxide.

WO 02/059046 describes the use of glow discharge technology to produce activated water that has germicidal activity, although rather low. This activation ensures the generation of e.g. peroxides in the water. However, the hydrogen peroxide and superoxide compounds of this activated water typically do not reach a level above about 0.05%. This, because prolonged exposure to an electrical discharge also degrades the formed hydrogen peroxide. This level of hydrogen peroxide is much too low to provide for an effective disinfectant.

Applicant found that by subjecting hydrogen peroxide solutions to a non-thermal electrical discharge, such as a plasma discharge or a corona discharge, it was possible to obtain an activated peroxide solution with a surprisingly higher biocidal activity than a common peroxide solution having the same $H_2O_2$ concentration. Surprisingly, the process time to obtain such an activated peroxide solution was substantially shorter than the time needed to obtain biocidal activated water by subjecting demineralized water to a non-thermal electrical discharge. In addition, with these shorter activation times no substantial degradation of the peroxide was observed.

Thus, in a first aspect, the present invention provides a process for the production of an activated peroxide solution by subjecting an aqueous $H_2O_2$ solution to a non-thermal electrical discharge, such as a non-thermal discharge plasma or a non-thermal corona discharge.

In the context of the invention, an activated peroxide solution is a solution obtainable by the process of the invention. Such activated peroxide according to this invention substantially differs from a common peroxide solution with the same $H_2O_2$ concentration that is obtained by simply adding the required amount of $H_2O_2$ to water. Next to $H_2O_2$, the activated peroxide solution may contain various species of super-oxides, ions and/or radicals.

An advantage of the use of a non-thermal electrical discharge in the method of the invention is that the electron density and ionization level in the resulting discharge is much lower than in thermal discharge plasma's such as lightning and arc discharges, enabling an efficient and controllable process.

A preferred method of producing the activated peroxide solution of the present invention comprises:

(a) placing a peroxide solution in the form of a layer in a chamber suitable for a non-thermal electrical discharge treatment, (b) positioning an electrode in the layer of (a) and an electrode with opposite potential in the gas phase above said layer, (c) generating a non-thermal electrical discharge in the chamber, and (d) subjecting the peroxide solution to the non-thermal electrical discharge, to obtain an activated peroxide solution.

The peroxide solution used in step (a), sometimes called herein "initial peroxide solution", may be tap water, potable water, demineralised, distilled and/or chemically pure water containing hydrogen peroxide. It is not necessary to supplement the initial peroxide solution with further additives, although additives may be present. The initial peroxide solution has a hydrogen peroxide concentration from 0.05% to 20% (w/w), preferably from 0.1% to 15%, more preferably from 0.1% to 10%, more preferably from 0.1 to 5%, most preferably from 0.4 to 3% (w/w).

Preferably, the water used for preparing the initial peroxide solution is demineralized, distilled and/or chemically pure water.

The initial peroxide solution may be at any pH, there is no preferred pH range prior to the treatment of the solution according to the invention. The pH of the initial aqueous solution may for instance vary depending on the type of water that is used for preparing the solution. In addition, the initial peroxide solution may have a pH below 7 because of acid that may be present in a commercial stock solution used to prepare the initial peroxide solution. Typically, the pH of the initial peroxide solution may be between 4 and 6.

After its preparation, the activated peroxide solution may suitably be diluted depending on the desired final $H_2O_2$ concentration.

The initial peroxide solution is placed in the form of a layer in a suitable chamber. Preferably, the layer has a depth from about 10 to 200 mm. The aqueous layer may be static or flowing, and oriented vertically, horizontally or inclined. In case of a vertical or inclined layer, the process is operated using a flow reactor, in which the water layer is flowing over one electrode and undergoing a discharge treatment from a discharge extending to the opposite electrode. Preferably, the layer is static and/or oriented horizontally, allowing the most convenient process. It is possible to bubble air through the aqueous layer to improve the activation process.

The depth of the aqueous layer should take into account that the distance between the top electrode and the liquid surface should not exceed a distance of about 15 mm.

The chamber may be any chamber, e.g. a cell or vessel, which is suitable for plasma production and treatment of an aqueous solution according to the invention.

Unlike electrodes (anode and cathode) are placed in the chamber. As used herein the term "unlike electrodes" refers to a set of electrodes of opposite potential, one of which is positive (anode) and one of which is negative (cathode). An electrode is positioned in the aqueous layer and an opposite electrode in the gas phase above the aqueous layer. Various embodiments for the set of unlike electrodes exist. For instance, the unlike electrodes may consist of one pair of anode and cathode or of multiple pairs of anode and cathode. It is also possible that one electrode of the unlike electrodes consists of multiple electrodes, discharging to one opposite electrode. Preferably, multiple anodes may discharge to one cathode.

In one embodiment, the positive electrode or anode is positioned in the gas phase above the surface of the liquid and the negative electrode or cathode is positioned below the surface of the liquid. It has been found that this provides a more stable operation and requires less current than vice versa. In this case, the surface of the liquid also acts as an electrode.

It is also possible that the lower electrode is positioned outside and underneath the reaction chamber.

The electrodes that can be used in accordance with the method of this invention can be comprised of any material that does not have a catalytic effect on hydrogen peroxide and super-peroxides and has high electrical conductivity. Examples of electrode materials include, but are not limited to, metals such as tungsten, titanium, tantalum, vanadium, zirconium, tin, stainless steel. Any other electrodes, which would be known to those in the art to satisfy the conditions necessary for water activation using a non-thermal electrical discharge, are also contemplated for use in the present invention.

In a preferred embodiment, the electrodes, more preferably the anode(s), are (is) of a pin shape and comprise(s) a relatively sharp tip, to ensure a high potential gradient, to enhance activation efficiency, to prevent arcing and to maintain a stable discharge. With a relatively sharp tip is meant that the point of the tip has at the most a diameter which is ⅓ of the diameter of the electrode, preferably a smaller diameter. More preferably the tip is a needle-sharp tip. The top angle of the pin-shaped electrode preferably is about 45°.

In a system, where two phases (fluid (gas) and liquid) are present, and an electric current is being formed between an electrode immersed in the liquid phase and an electrode placed into the gas phase, the boundary of the two phases is of special importance because this is where intensive physical and chemical transformations are taking place, which in turn drive the reactions taking place in the hydrogen peroxide solution. Thus, the thickness of the water layer and the distance between electrodes are critical for providing uniform treatment the aqueous layer, and thus to increase efficiency of activation of the aqueous layer. The distance between the electrode in the gas phase (top electrode) and the liquid surface preferably is from about 3-15 mm, more preferably from about 3-12 mm, most preferably about 8-10 mm.

The pressure in the chamber should enable the formation of a uniform non-thermal electrical discharge and may be atmospheric pressure or a suitable under-pressure. The choice of pressure conditions may depend on the other process parameters. The formation of a uniform non-thermal electrical discharge may be facilitated by creating an under-pressure atmosphere in the chamber, preferably a moderate under-pressure of about $1-5\times10^4$ Pa, more preferably an under-pressure of about $1.5-2.5\times10^4$ Pa.

The gas phase may consist of any suitable gas or mixture of gases, such as air and/or a noble gas. It is preferred to include a gas in the gas phase that reacts with the plasma and the peroxide solution, such as $NO_x$, $CO_2$ or $O_2$.

The initial peroxide solution is subjected to the non-thermal electrical discharge to obtain an activated peroxide solution.

Important elements of the process to generate the non-thermal electrical discharge and to treat the initial peroxide solution with a non-thermal electrical discharge are 1) to provide conditions which prevent the discharge from becoming a thermal discharge (e.g. an arc), 2) to provide conditions which bring the discharge into intimate contact with the aqueous surface so that active radicals can form new substances, and 3) to use configurations which create large areas of electrical discharge, enabling the treatment of large throughput volumes.

The non-thermal electrical discharge may preferably be a glow discharge plasma or a corona discharge.

The glow discharge plasma or the corona discharge may be an alternating current (AC) at high frequency, commonly referred to as radio frequency (RF), or direct current (DC) discharge. In a situation where the lower electrode in fact is an aqueous solution, it is preferred to use the DC mode.

In a preferred embodiment, the glow discharge plasma or the corona discharge is operated in a pulsed mode. This allows higher instantaneous powers to be applied without excessively heating the aqueous layer. In the pulsed mode, the preferred frequency is in the range of 50-5,000 Hz. Pulsed glow discharge plasma's and pulsed corona discharges are discharge types that run reliably at low and at high temperatures, in various gasses and with a wide range of compositions.

A very particular advantage of pulsed corona discharges is the fact that a highly reactive streamer discharge medium is created, while the bulk gas is at ambient temperature and pressure. Therefore, pulsed corona promises higher efficiency than other advanced oxidation processes.

Compared with AC and radio frequency (RF) discharges, pulsed DC discharges have the advantage of causing less electromagnetic interference and providing the possibility to control the water temperature with the pulse duty cycle without changing the plasma parameters during the pulse-on times.

In another preferred embodiment, the glow discharge plasma, preferably the DC glow discharge plasma, more preferably the pulsed DC glow discharge plasma is induced by a corona, preferably a pulsed corona. The plasma created by corona induction is a uniform and very stable, low temperature glow discharge plasma. The combination of a corona discharge and a glow discharge also provides for a highly controllable process and a highly predictable outcome of the end product quality.

Thus, it is preferred to use a pulsed DC glow discharge plasma induced by a pulsed corona, a so-called pulsed corona induced pulsed DC glow discharge plasma process. More preferably, a pulsed corona induced low frequency pulsed DC glow discharge plasma is used. Compared to pure DC or (very) high frequency DC discharges, low frequency pulsed DC discharges have the advantage of producing fewer arcs and creating a higher electron impact. This is important for producing an activated peroxide solution with a strong and long lasting biocidal activity according to this invention. A low frequency in this regard is about 50-5,000 Hz, preferably 100-1,000 Hz.

The pulsed corona induced pulsed DC glow discharge plasma process is performed at a low frequency, at a temperature below the boiling point of water and at a current, voltage and pressure sufficient to produce a stable discharge plasma, whereby the discharge plasma extends to the surface of the liquid. It is preferred to use a higher voltage than known in the art and a relatively low current, in order to avoid excessive heating of the water and to enable a more efficient formation of the biocidal solution. It shows from experience that heating of the liquid results in a destruction of the biocidally active components and actually decreases activation efficiency.

The low frequency pulsed DC glow discharge plasma is induced by a pulsed corona discharge to electrically ionize the gas above the liquid and enable the formation of ions in the liquid. The induction voltage of the corona discharge is about 5000-20,000 V. The process starts with an initial low operating current as the non-ionized air and water form a significant dielectric barrier. Within several minutes, the current is slowly increased from about 0 mA to 100-200 mA once ionization has fully occurred, while the voltage is decreased to preferably 500-10,000 V, more preferably to 1000-2500 V.

The current per electrode is maintained at a rather low level in the range of 20-500 mA, preferably 100-300 mA, more preferably 100-200 mA, for a period sufficient to produce the activated peroxide solution. This period typically will be dependent on parameters like the volume of the treated solution and the current density. The voltage is maintained at a level sufficient to sustain a stable discharge, usually about 500-10,000 V, preferably 500-5000 V, more preferably 1000-2500 V.

It was surprisingly found that the time period needed to produce a biocidal activated peroxide solution was considerably shorter than the period needed to activate demineralized water without added hydrogen peroxide, around a quarter to half of the time period to activate water. In addition, the process of the invention appeared to be more stable and predicable when using a peroxide solution as compared to using water.

The present invention shows that it is possible to produce a stable plasma by using pin shaped electrodes (as opposed to plate or annular electrodes commonly used in the art) to prevent arcing and to form a uniform and stable plasma, using a relatively low clock frequency and a corona induced plasma to electrically ionize the gas atmosphere above the water and form ions in the water, and most importantly using a relatively low current. By altering the pulse duty cycle and frequency, it was possible to control the process and heat up of the liquid and alter the properties of the treated peroxide solution. The low current used and low clock frequency make the method of the invention very cost efficient and enable an economically attractive production of an activated peroxide solution.

The properties of the activated peroxide solution may be varied by altering the current, the voltage, the treatment time, the pressure and/or the electrode distance. Varying the current, electrode distance and/or pressure results in differences in current density, which is in general an important parameter for the extent of activation. Current density is a measure of the current per unit surface area of the plasma touching the liquid. The higher the current density at a constant volume, the more the liquid is activated.

In addition, the treatment time and the volume of treated liquid are important variables. The longer the treatment time at a constant volume or the lower the volume at a constant treatment time, the more the solution is activated.

It is further important to keep the process relatively cool, for instance to keep the temperature at a value of at the most 40° C., preferably at 30-40° C., more preferably at 34-40° C.

In a preferred embodiment, the process of the invention is performed in a stepwise fashion, wherein the aqueous solution is subjected to at least two successive series of an activation and subsequent cooling step. Thus, the activation and cooling steps may conveniently be performed several times, e.g 2 to 5 times, until the desired parameters of the peroxide solution are obtained. In this way, a higher concentration of peroxides and super-oxides, a higher concentration of biocidally active ions, a higher ORP and a lower pH are obtained, resulting in a higher biocidal activity.

The chemical reactivity of a non-thermal electrical discharge such as a glow discharge plasma or a corona discharge is based on the fact that the electric field strength at the head of the discharge streamer is extremely high. Corona and glow discharge plasmas produce hydroxyl radicals and hydrogen atoms in aqueous solutions from the dissociation and ionization of water molecules. In a humid gas phase, corona and glow discharge plasmas additionally create radicals, ions and metastables from the dissociation and ionization of the gas phase molecules or atoms. In humid air, the following main oxidizer species are produced: hydroxyl radicals, ozone, atomic oxygen, singlet oxygen and hydroperoxyl radicals. Also, small amounts of nitrogen oxides like $NO_x$ and $N_2O$ are formed. By exposure of deionized water to corona or glow discharge plasmas, the electrical conductivity significantly increases. This is likely due to mainly carbonate and nitrate ions, originating from carbon(di)oxides and nitrogen(di)oxides, which are produced by the corona or the glow discharge plasma in air. Corona-induced anode metal sputtering is theoretically possible, but metals have not been identified in any significant quantities.

Through these methods, it has been determined that, during the initial stages of treatment of the peroxide solution by an electrical discharge process, a number of transformations occurs, including the formation of ions, excited water molecules and the formation of secondary electrons. These chemical reactions and actively formed radicals characterize the reactivity of the activated peroxide solution produced.

In one embodiment of the invention, an additive may be added to the initial peroxide solution. Preferably, the additive is not destroyed by the non-thermal electrical discharge. Suitable additives may be an acid, a base and/or a salt. Preferred salts are chloride salts such as NaCl and/or KCl.

In a second aspect, the present invention provides an activated peroxide solution that shows certain unique features as described herein in the specification.

As compared to a common peroxide solution, the conductivity of the activated peroxide solution of the invention is increased due to the presence of ions. The activated peroxide solution also has a higher oxidation-reduction potential (ORP) as well as a lower pH as compared to a common peroxide solution. Furthermore, the activated peroxide solution according to the invention has a biocidal activity against a broad spectrum of micro-organisms, including gram positive and/or gram negative bacteria and fungi.

The characterizing features of the activated peroxide solution wherein it differs from a common peroxide solution, like conductivity, pH, ORP, are to be seen as features that are measurable under conditions wherein the activated peroxide solution is in a form essentially without the presence of additional compounds in the activated peroxide solution. "Additional compounds" are compounds that are not formed by the activation process according to the invention. The phrase "in a form essentially without the presence of additional compounds" means that the activated peroxide solution is in a form wherein it does not contain additional compounds in such a concentration that they substantially affect the characterizing features of the activated peroxide solution. Preferably, the characterizing features of the activated peroxide solution are measurable when the solution is in its purest possible form, i.e. is obtainable from an initial peroxide solution prepared by using demineralized, distilled or chemically pure water as a solvent.

Since the initial peroxide solution may be prepared by diluting a commercial concentrated hydrogen peroxide solution to the desired peroxide concentration, the initial peroxide solution may contain minor quantities of additives that are present in the commercial peroxide solution. Some or all of these additives may be destroyed by the activation process.

The features of the activated peroxide solution wherein it differs from a common peroxide solution thus are to be seen as inherent features of the activated peroxide solution in a form essentially without the presence of additional compounds and are not to be seen as features that are due to the presence of additional compounds that are deliberately added to the solution and/or accidentally present without being the result of the process of the invention.

In particular, the present invention provides an activated peroxide solution characterized by a peroxide content in the range of 0.05% to 20% (w/w), a low pH in the range of 2 to 4, an ORP in the range of 400 to 600 mV, and an electrical conductivity in the range of 100 to 500 μSiemens/cm, preferably 100-450 μSiemens/cm, for a solution with a peroxide content in the range of 0.05% to 0.5%(w/w), an electrical conductivity in the range of 100 to 450 μSiemens/cm, preferably 100-350 μSiemens/cm, for a solution with a peroxide content in the range of 0.1% to 5%(w/w) and an electrical conductivity in the range of 100 to 350 μSiemens/cm for a solution with a peroxide content in the range of 5% to 20% (w/w). The activated peroxide solution has a biocidal activity against a broad spectrum of micro-organisms.

The features of the activated peroxide solution are commonly determined by standard, commercially available methods and equipment, and are preferably measured at room temperature (20° C.).

The peroxide concentration is determined by a potassium permanganate titration procedure and the devices used for the measurement of pH, ORP and conductivity are a WTW 537, a Testo 230 ORP and a HANNA EC device, respectively.

The hydrogen peroxide content of the activated peroxide solution preferably is 0.1 to 15%, more preferably 0.1 to 10%, even more preferably 0.1 to 5%, most preferably 0.4 to 3%.

The pH of the biocidal solution is decreased as compared to the pH of the initial aqueous solution, due to the activation process. The decreased pH of the activated peroxide solution according to the invention thus is not due to the addition of an acid. The acidity of the biocidal solution of the invention is not compensated, at least not fully compensated, by the presence of a "regular" anion, i.e. an anion that normally functions as a counter ion for the acid cation $H^+$ or $H_3O^+$, for example nitrate, sulphate, chloride, and the like.

The pH of the activated peroxide solution preferably is 2.5-4, preferably 2.5-3.5, most preferably 2.5-3.

Furthermore, the ORP of the biocidal solution is increased as compared to the ORP of the initial peroxide solution, due to the activation process. The ORP of the activated peroxide solution preferably is 400-500, more preferably 420-490 mV. The ORP is generally also higher than that of commonly prepared acidic peroxide solutions of similar peroxide concentration and pH.

Furthermore it appears that the conductivity of the activated peroxide solution is substantially lower than the conductivity of commonly prepared acidic hydrogen peroxide solutions having the same pH, indicating that the ionic strength of the activated peroxide solution is relatively low and the acidic nature has been caused by a very specific reaction mechanism in the activation process. Preferably, the lower limit of the conductivity of the activated peroxide solution is 150 μSiemens/cm.

The biocidal activity of the activated peroxide solution is such that it provides at least a log 4 reduction using a European Norm EN 1040 conform assay against *Escherichia coli*, *Rhodotorula rubra*, *Pseudomonas aeruginosa* and/or *Salmonella typhimurium* for a 5 minute contact time.

Sometimes the water that is used to prepare the initial peroxide solution to be subjected to the activation process according to the invention may contain chlorine-containing compounds, such as when using tap water or when adding chlorine salts to the solution before activation. The pH of the obtained activated peroxide solution may initially be higher than 4 and a prolonged activation may be necessary to reach a pH lower than 4. It appears that certain micro-organisms are even more sensitive to the biocidal activated peroxide solution when tap water is used or when additionally chlorine-salts are added to the solution before activation.

In one embodiment, the activated peroxide solution has substantially no available free chlorine (AFC) content. Such a solution is advantageously obtainable by the process of the first aspect using demineralized, distilled and/or chemically pure water.

In particular, the activated peroxide solution of the second aspect is obtainable by the process of the first aspect.

The application of a non-thermal electrical discharge according to the invention leads to fundamental structural changes in an aqueous peroxide solution, providing the resulting activated peroxide solution with enhanced biocidal activity. Surprisingly, the biocidal activity of the activated peroxide solutions of the present invention is substantially higher than that of a common peroxide solution with the same peroxide content but prepared with normal water. Even if a peroxide solution is prepared with water subjected to the process of the invention, the biocidal activity thereof is lower than that of the activated peroxide solution according to the invention.

Other additives may be added to the activated peroxide solution after its preparation by the method of the invention in order to increase its biocidal activity or to provide the activated peroxide solution with properties suitable for its use. Examples of such additives are silver salts, e.g., silver nitrate or silver chloride, or colloidal silver; zinc salts, e.g. zinc chloride, zinc lactate, or zinc oxide; chlorhexidine; anionic, cationic, non-ionic and/or amphoteric surfactants; emulsifiers; hydrotropes; glycerol; chelating agents; alcohols; acids (organic or inorganic); bases; fragrances; coloring chemicals; or surface tension decreasing agents.

Preferably, the activated peroxide solution is stabilized with commercially available compounds known to stabilize hydrogen peroxide solutions, such as (Colloidal) Stannates, Citric Acid, Ethylenediaminetetraacetic acid (EDTA), Acetanilide, various types of Phosphonates such as the Dequest Phosphonates available from Solutia, stabilizers such as Trisodium Ethylenediamine Disuccinate available from Octel as OctaQuest E30 or A65, or other Cation Sequestering Agents.

The present invention thus provides a composition comprising an activated peroxide solution of the invention and optional additives, as defined above.

In another aspect, the present invention relates to the use of the activated peroxide solution of the invention or compositions containing said activated peroxide solution for any purpose where disinfecting and/or sanitizing and/or cleaning and/or bleaching and/or preservative activity is required, including, but not limited to, use as a bactericidal and sterilization liquid, and as cleaning, disinfection and sanitization agent.

In particular, the activated peroxide solution of the invention or composition containing it may be used for those applications where it is important to obtain disinfecting and/or sanitizing and/or cleaning and/or bleaching and/or preservative activity with the mildest agents possible, for instance domestic use, medical use, personal care, food, clean rooms, etc. Also for applications where no or scarce rinsing after application is preferred, or where the solution may come into contact with food. As the activated peroxide solution in its basic form does not contain any acids or salts, no environmentally burdening or food-contaminating residues are present. This enables the use of the solution in situations where environmentally friendly products are preferred.

Since the activated peroxide solution is non-irritating, has no odors or volatile gasses, and is skin friendly, it is also optimal for situations where users do not wear any protective clothing, in cases where worker-safety has high priority or for personal application like wound disinfection or prevention of gingivitis.

The present invention also relates to the use of the activated peroxide solution in specific devices such as spray devices, e.g. spray bottles, aerosol cans, aerosol generation devices for room disinfection, and by application in the form of dipping.

The hydrogen peroxide concentration of a solution or composition for final use is preferably 0.1-15% (w/w), more preferably 0.1-10%, even more preferable, 0.1-5%, most preferably 0.4-3%. To obtain such a solution or composition for final use, it is preferred to dilute the activated peroxide solution of the invention as less as possible.

In particular, the present invention discloses a method for disinfecting a substrate comprising contacting the substrate with an effective amount of the biocidal solution or composition according to the invention. The substrate may be any surface, space, material, medical instrument or device, hospital equipment, surface of walls, ceilings and/or floors, preferably a substrate wherein the presence of gram positive and/or gram negative pathogenic bacteria is suspected.

EXAMPLES

Example 1

To 600 milliliters of chemically pure distilled water having a pH of 6.7 and an electrical conductivity of less than 0.1 µS/cm, concentrated hydrogen peroxide was added to reach a 1.6% hydrogen peroxide content, and the solution was subjected to a pulsed corona induced pulsed DC glow discharge plasma process. The pH of the solution before activation was 5.8. The solution was put in a 1 L double walled water cooled vessel. One electrode was submersed in the aqueous solution and three pin shaped electrodes were placed approximately 10 mm above the liquid surface. Pressure was lowered and the reactor chamber cooled with cooling water. The water was then processed by pulsed corona induced low frequency pulsed DC plasma discharge under the following conditions: the current was increased from 0 mA to 100 mA in 5 minutes, the current was maintained on 100-120 mA for another 25 minutes of treatment, the pulsed corona induction voltage was 10 kV, the pulsed DC plasma voltage was between 1500 and 1700 Volt, the frequency was 100 Hz, the pressure in the reaction chamber was $1.5 \times 10^4$ Pa.

The resulting ORP of the solution was 494 mV, the pH of the solution was 2.92, and the gross concentration of hydrogen peroxide and super-peroxide compounds was 1.6%.

Biocidal Activity

The activated peroxide solution exhibited very significant biocidal activity. In a controlled bactericidal suspension test conform European Norm for testing of basic bactericidal activity of chemical disinfectants and antiseptics EN 1040, a 1 ml McFarland standard 0.5 ($10^8$ microorganisms per ml) was mixed 1:8 with the activated peroxide solution and 1 ml milli-Q water. After 10 minutes, *Staphylococcus aureus* was killed 100%, while *Escherichia coli, Salmonella typhimurium, Rhodotorula rubra* and *Pseudomonas aeruginosa* were all killed 100% already after 5 minutes. The norm is typically passed with at least a log 5 reduction at 5 minutes.

In this test, a control was ran with a 1.6% common hydrogen peroxide solution. The results were that after 5 minutes none of the samples showed a 100% kill. For example, Salmonella typhimurium exhibited only a 70% reduction after 5 minutes and Staphylococcus aureus exhibited only a 50% reduction after 20 minutes and none after 5 minutes. This indicates that the activated peroxide solution of this invention has a significantly higher biocidal activity than a comparable common hydrogen peroxide solution.

Example 2

A 1,3% of hydrogen peroxide solution was treated as in Example 1, under the following conditions: the current was increased from 0 mA to 100 mA in 5 minutes, the current was maintained on 100-140 mA for another 45 minutes of treatment, the pulsed corona induction voltage was 10 kV, the pulsed DC plasma voltage was between 1500 and 2000 Volt, pressure in the reaction chamber was $1.5 \times 104$ Pa.

The resulting ORP of the solution was 502 mV, the pH of the solution was 2.85, and the gross concentration of hydrogen peroxide and super-peroxide compounds was 1.25%.

Biocidal Activity

The solution exhibited very significant biocidal activity. In a controlled bactericidal suspension test conform European Norm for chemical disinfectants and antiseptics 1276. (EN 1276: Quantitative suspension test for the evaluation of bactericidal activity of chemical disinfectants and antiseptics used in food, industrial, domestic, and institutional areas: test method and requirements), a 1 ml McFarland standard 0.5 ($10^8$ microorganisms per ml) was mixed 1:8 with the activated peroxide solution and 1 ml milli-Q water. To this suspension a protein load was added according to the EN 1276 procedures to simulate unclean practical conditions. To provide for a clean condition 0.3% Bovine Albumin was added and for a dirty condition 3% Bovine Albumin.

The test results are presented in Table 1 below. Several bacteria types show greater than log 5 reduction within 5 minutes, which is the test norm according standard EN 1276, while some even reach log 5 reduction after only 1 minute, at only a 1,2% hydrogen peroxide concentration, a level of hydrogen peroxide that is very low compared to biocidal solutions described in the prior art.

Example 3

A volume of 500 milliliters of a 1% hydrogen peroxide solution was treated with a pulsed corona discharge. The conductivity of the starting solution was 17.8 microSiemens/cm, the pH 4.5 and the ORP 340 mV. The electrode distance was 10 mm, the pressure in the vacuum chamber was lowered to maintain a stable corona discharge. The applied corona voltage was 10.4 kV and the current was kept at approximately 1.5-1.8 mA. After 45 minutes of treatment with 3 electrodes, the solution measured the following parameters: Conductivity 123.3 microSiemens/cm, the pH was 3.2 and the ORP 445.

The corona treated solution was then tested against several strains of bacteria and compared to untreated solutions of 1% hydrogen peroxide. Applicant found the following results:

*E. coli* was reduced with log 4 after 1 minute and with log 5 after 5 minutes, while there was no countable reduction observed with standard 1% hydrogen peroxide. *Lysteria* was reduced with log 4 after 5 minutes, while there was no countable reduction observed with a standard 1% hydrogen peroxide solution. *Corynebacterium minitissium* was reduced with log 4 after 5 minutes and showed no countable reduction with a standard 1% hydrogen peroxide solution. Results with *Enterobacter cloacea* showed a significant difference in reduction between the two solutions as well.

TABLE 1

| Type of Microorganism | Contact time 1 min Clean | | Contact time 1 min Dirty | | Contact time 5 min Clean | | Contact time 5 min Dirty | | Contact time 15 min Clean | | Contact time 15 min Dirty | | Contact time 20 min Clean | | Contact time 20 min Dirty | |
|---|---|---|---|---|---|---|---|---|---|---|---|---|---|---|---|---|
| | 1 | 2 | 1 | 2 | 1 | 2 | 1 | 2 | 1 | 2 | 1 | 2 | 1 | 2 | 1 | 2 |
| E. coli | >5 | >5 | >5 | >5 | >5 | >5 | >5 | >5 | >5 | >5 | >5 | >5 | >5 | >5 | >5 | >5 |
| S. aureus | <5 | <5 | <5 | <5 | <5 | <5 | <5 | <5 | >5 | >5 | <5 | <5 | >5 | >5 | >5 | >5 |
| E. Hirae | <5 | <5 | <5 | <5 | <5 | <5 | <5 | <5 | >5 | >5 | >5 | >5 | >5 | >5 | >5 | >5 |
| P. aeruginosa | >5 | >5 | <5 | <5 | >5 | >5 | >5 | >5 | >5 | >5 | >5 | >5 | >5 | >5 | >5 | >5 |
| S. pyogenes | <5 | <5 | <5 | <5 | >5 | >5 | <5 | <5 | >5 | >5 | >5 | >5 | >5 | >5 | >5 | >5 |
| P. vulgaris | >5 | >5 | >5 | >5 | >5 | >5 | >5 | >5 | >5 | >5 | >5 | >5 | >5 | >5 | >5 | >5 |
| S. typhimurium | <5 | <5 | <5 | <5 | >5 | >5 | >5 | >5 | >5 | >5 | >5 | >5 | >5 | >5 | >5 | >5 |
| E. cloacae | >5 | >5 | >5 | >5 | >5 | >5 | >5 | >5 | >5 | >5 | >5 | >5 | >5 | >5 | >5 | >5 |
| R. rubra | >5 | >5 | >5 | >5 | >5 | >5 | >5 | >5 | >5 | >5 | >5 | >5 | >5 | >5 | >5 | >5 |
| C. albicans | <5 | <5 | <5 | <5 | >5 | >5 | >5 | >5 | >5 | >5 | >5 | >5 | >5 | >5 | >5 | >5 |

Example 4

Comparison of the Biocidal Activity of the Activated Peroxide Solution of the Invention With an Acidic Aqueous Solution of Hydrogen Peroxide In the prior art, a combination of hydrogen peroxide and a specific acid is proposed, because hydrogen peroxide as such is a relatively ineffective disinfectant. By adding an acid, the solution is generally more stable and also more effective as bactericidal, but still killing times of microorganisms are in unpractical ranges.

We now show that both an untreated hydrogen peroxide solution of exactly the same hydrogen peroxide concentration as the activated peroxide solution, as well as a hydrogen peroxide solution to which acid is added in order to enhance efficacy, again of exactly the same hydrogen peroxide concentration as the activated solution, have both a significantly less bactericidal effect than a hydrogen peroxide solution treated by pulsed corona induced pulsed DC plasma discharge.

We have tested a activated hydrogen peroxide solution of the invention to which 1.5% hydrogen peroxide was added prior to treatment with pulsed corona induced low frequency pulsed DC plasma discharge and a standard, commercially available (untreated) 1.5% hydrogen peroxide solutions on 6 bacterial strains: *Salmonella typhimurium, E. coli, Pseudomonas aeruginosa, Staphylococcus aureus, Enterobacter cloacae* and *Lysteria monocytogenes*. The 1.5% hydrogen peroxide solution was treated for 30 minutes and has a pH of 3.1 and an ORP of 452. The results in Table 2 below show that the biocidal effect of the activated peroxide solution (upper results) is greatly enhanced by the activation process.

TABLE 2

Biocidal activity of solutions containing hydrogen peroxide

| Bacteria Type | Start MacFarland | 1 Min. | 2 Min. | 3 Min. | 4 Min. | 5 Min |
|---|---|---|---|---|---|---|
| 1.5% Hydrogen peroxide solution treated with Pulsed Corona Induced Pulsed DC plasma Discharge | | | | | | |
| Salmonella typhimurium | 1.0 | >1000 | >1000 | >500 | 148 | 26 |
| E. coli | 1.0 | >1000 | >1000 | 128 | 1 | 0 |
| P. aeruginosa | 0.5 | 10 | 0 | 0 | 0 | 0 |
| S. aureus | 1.0 | >1000 | >1000 | >1000 | >500 | 500 |
| Enterobacter cloacae | 0.5 | >1000 | >1000 | >1000 | >500 | 68 |
| Lysteria monocytogenes | 0.5 | >1000 | >1000 | >1000 | >1000 | >500 |
| 1.5% Hydrogen Peroxide solution added with phosphoric acid to pH 3 | | | | | | |
| Salmonella typhimurium | 1.0 | >1000 | >1000 | >1000 | >1000 | >1000 |
| E. coli | 1.0 | >1000 | >1000 | >1000 | >1000 | >500 |
| P. aeruginosa | 0.5 | 268 | 26 | 7 | 0 | 0 |
| S. aureus | 0.5 | >1000 | >1000 | >1000 | >1000 | >500 |
| Enterobacter cloacae | 0.5 | >1000 | >1000 | >1000 | >1000 | >1000 |
| Lysteria monocytogenes | 0.5 | >1000 | >1000 | >1000 | >1000 | >1000 |

It is shown from empirical tests that an increased ORP and a decreased pH together are important parameters explaining the significantly enhanced biocidal effect of the activated peroxide solutions of this invention. It was experimentally established that the ORP, pH and conductivity of an activated peroxide solution substantially differ from those of a commercially available hydrogen peroxide solution with the same $H_2O_2$ concentration.

0.1% $H_2O_2$ shows a pH of approximately 4.9, a conductivity of 20 μS/cm and an ORP of 355 mV, compared to a pH of approximately 3.1, a conductivity of 248 μS/cm and an ORP of 452 mV of a solution of similar $H_2O_2$ concentration, but activated with the method of this invention.

0.5% $H_2O_2$ shows a pH of approximately 4.6, a conductivity of approximately 21 μS/cm and an ORP of 374 mV, compared to a pH of approximately 3.2, a conductivity of 255 μS/cm and an ORP of 448 mV of a solution of similar $H_2O_2$ concentration, but activated with the method of this invention.

1% $H_2O_2$ shows a pH of approximately 4.4, a conductivity of 30 μS/cm and an ORP of 390 mV, compared to a pH of approximately 3.1, a conductivity of 212 μS/cm and an ORP of 472 mV of a solution of similar $H_2O_2$ concentration, but activated with the method of this invention.

3% $H_2O_2$ shows a pH of approximately 3.9, a conductivity of 60 μS/cm and an ORP of 411 mV, compared to a pH of approximately 2.9, a conductivity of 328 μS/cm and an ORP of 468 mV of a solution of similar $H_2O_2$ concentration, but activated with the method of this invention.

5% $H_2O_2$ shows a pH of approximately 3.7, a conductivity of 90 μS/cm and an ORP of 428 mV, compared to a pH of approximately 2.9, a conductivity of 288 μS/cm and an ORP of 469 mV of a solution of similar $H_2O_2$ concentration, but activated with the method of this invention.

10% $H_2O_2$ shows a pH of approximately 3.3, a conductivity of 110 μS/cm and an ORP of 446 mV, compared to a pH of approximately 2.8, a conductivity of 238 μS/cm and an ORP of 485 mV of a solution of similar $H_2O_2$ concentration, but activated with the method of this invention.

Example 5

Hydrogen peroxide solutions containing different amounts of hydrogen peroxide (from 0.05-20%) were subjected to a pulsed corona induced pulsed DC glow discharge plasma process. The process conditions were a current between 100-130 mA per electrode, an electrode distance around 10 mm, the pulsed corona induction voltage was 10 kV, the pulsed DC plasma voltage was between 1500 and 2000 Volt, and the pressure in the reaction chamber was $3 \times 10^4$ Pa. The pH, conductivity and ORP values of the resulting activated solutions are shown in Table 3, as well as the values of the solutions prior to activation.

TABLE 3

| $H_2O_2$ % | pH | | Conductivity μSiemens/cm | | ORP mV | |
|---|---|---|---|---|---|---|
| | before | after | before | after | before | after |
| 0.05 | 5.1 | 2.8 | 3 | 430 | 309 | 451 |
| 0.5 | 5.4 | 2.6 | 10 | 420 | 314 | 460 |
| 1 | 4.9 | 2.6 | 5 | 380 | 337 | 480 |
| 2 | 4.8 | 2.8 | 7 | 338 | 340 | 478 |
| 5 | 4.8 | 2.8 | 11 | 270 | 338 | 485 |
| 7.5 | 4.8 | 2.6 | 13 | 310 | 333 | 484 |
| 10 | 4.8 | 2.7 | 14 | 250 | 350 | 490 |
| 15 | 4.6 | 2.6 | 15 | 140 | 369 | 492 |
| 20 | 4.6 | 2.7 | 20 | 115 | 372 | 488 |

It further appeared that the activated peroxide solution shows a significantly lower conductivity than peroxide solutions in which an acid is added to lower the pH to the same value as is obtained upon activation. Hydrogen peroxide solutions containing 1, 2 and 5% $H_2O_2$ and having a pH of 2.8 typically showed a conductivity of 600-900 μS/cm. This phenomenon occurred while using any acid, whereby the effect is most dramatic with stronger acids.

The invention claimed is:

1. An activated biocidal aqueous solution containing 0.1 to 20% (w/w) hydrogen peroxide obtained by subjecting a solution of 0.1 to 20% (w/w) hydrogen peroxide in demineralized, distilled or chemically pure water to a non-thermal electrical discharge process,
   wherein said biocidal solution has a pH in the range of 2 to 4, an oxidation-reduction potential (ORP) in the range of 400 to 600 mV, and the solution when having a peroxide content in the range of 0.1% to 5% (w/w) has a conductivity in the range of 100 to 450 μSiemens/cm, and the solution when having a peroxide content in the range of 5% to 20% (w/w) has a conductivity in the range of 100 to 350 μSiemens/cm.

2. The activated biocidal aqueous solution of claim 1, wherein the pH, ORP and conductivity are measurable under conditions essentially without the presence of additional compounds in the solution.

3. The activated biocidal aqueous solution of claim 1, with substantially no available free chlorine (AFC) content.

4. The activated biocidal aqueous solution of claim 1, having a hydrogen peroxide content of 0.1 to 15%.

5. The activated biocidal aqueous solution of claim 1, having a pH of 2.5-4.

6. The activated biocidal aqueous solution of claim 1, having an ORP of 400-500 mV.

7. The activated biocidal aqueous solution of claim 1, which has a biocidal activity against a broad spectrum of micro-organisms, including gram positive and/or gram negative bacteria and fungi.

8. The activated biocidal aqueous solution of claim 1, wherein said aqueous solution provides at least a log 4 reduction using a European Norm EN 1040 conform assay against Escherichia coli, Rhodotorula rubra, Pseudomonas aeruginosa or Salmonella typhimurium for a 5 minute contact time.

9. The activated biocidal aqueous solution of claim 1, wherein the non-thermal electrical discharge process is a glow discharge plasma or a corona discharge, preferably a pulsed DC glow discharge plasma, more preferably a pulsed corona induced pulsed DC glow discharge plasma.

10. A composition comprising an activated biocidal solution according to claim 1 and an additive.

11. The composition of claim 10, wherein the additive is selected from silver salts; colloidal silver; zinc salts; chlorhexidine; anionic, cationic, non-ionic and/or amphoteric surfactants; emulsifiers; hydrotropes; glycerol; stannates; chelating agents; alcohols; acids; bases; fragrances; coloring chemicals; and/or surface tension decreasing agents.

12. A process for the preparation of an activated aqueous solution according to claim 1 comprising:
(a) placing an aqueous solution containing 0.01 to 20% hydrogen peroxide in the form of a layer in a chamber suitable for a non-thermal electrical discharge treatment,
(b) positioning an electrode in the layer of (a) and an electrode with opposite potential in the gas phase above said layer,
(c) generating a non-thermal electrical discharge in the chamber, and
(d) subjecting the peroxide solution to the non-thermal electrical discharge to obtain an activated peroxide solution.

13. The process of claim 12, wherein the non-thermal electrical discharge is a glow discharge plasma or a corona discharge.

14. The process of claim 13, wherein the glow discharge plasma or the corona discharge is operated in a pulsed mode and/or is a direct current (DC) discharge (plasma).

15. The process of claim 13, wherein the glow discharge plasma, preferably the DC glow discharge plasma, is induced by a corona, preferably a pulsed corona.

16. The process of claim 15, wherein the glow discharge plasma is a pulsed corona induced pulsed DC glow discharge plasma, preferably performed at a frequency in the range of 50-5,000 Hz, more preferably in the range of 100-1,000 Hz.

17. A method for at least one of disinfecting, sanitizing, cleaning, and bleaching a substrate comprising contacting the substrate with an effective amount of the activated biocidal aqueous solution of claim 1.

18. The method according to claim 17, wherein said substrate is any surface, space, material, medical instrument or device, hospital equipment, or surface of walls, ceilings and floors, wherein the presence of gram positive and/or gram negative pathogenic bacteria is suspected.

19. The method according to claim 17, wherein the contracting is by applying the solution from a spray device, aerosol can, aerosol generation device, for room disinfection or in the form of dipping.

20. The activated biocidal aqueous solution of claim 1, having a hydrogen peroxide content of 0.1 to 10%.

21. The activated biocidal aqueous solution of claim 1, having a hydrogen peroxide content of 0.1 to 5%.

22. The activated biocidal aqueous solution of claim 1, having a hydrogen peroxide content of 0.4 to 3%.

\* \* \* \* \*